US00PP32345P2

(12) United States Plant Patent
Olesen

(10) Patent No.: US PP32,345 P2
(45) Date of Patent: Oct. 20, 2020

(54) HYBRID TEA ROSE PLANT NAMED 'POULREN031'

(50) Latin Name: ***Rosa* hybrid**
Varietal Denomination: Poulren031

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Frendensborg (DE)

( * ) Notice: Subject to any disclaimer, the term of this patent is extended or adjusted under 35 U.S.C. 154(b) by 0 days.

(21) Appl. No.: 16/602,243

(22) Filed: Sep. 4, 2019

(51) Int. Cl.
*A01H 5/02* (2018.01)
*A01H 6/74* (2018.01)

(52) U.S. Cl.
USPC ..... Plt./139

(58) Field of Classification Search
USPC ..... Plt./101, 130, 139
See application file for complete search history.

*Primary Examiner* — Susan McCormick Ewoldt

(57) ABSTRACT

A new garden rose plant of the Hybrid Tea class which has abundant, orange red flowers and attractive foliage. This new and distinct variety has shown to be uniform and stable in the resulting generations from asexual propagation.

2 Drawing Sheets

Botanical designation: *Rosa* hybrid.
Variety denomination: 'Poulren031'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulren031', originated as a single seedling from the stated cross.

The new variety may be distinguished from its male pollen parent and female seed parent primarily by the following characteristics. The male pollen parent plant has orange flowers while the new variety has orange red flowers. The female seed parent plant has red flowers while the new variety has orange red flowers.

The objective of the hybridization of this rose variety was to create a new and distinct variety with unique qualities, such as:

1. Uniform and abundant orange red flowers;
2. Vigorous, but compact growth when propagated on its own roots;
3. Exceptional disease resistance; and
4. Perfumed flowers.

This combination of qualities is not present in previously available commercial cultivars of this type, known to the inventor, and distinguish 'Poulren031' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulren031' was selected in the spring of 2013 by the inventor as a single plant from the progeny of the aforementioned hybridization.

Asexual reproduction of 'Poulren031' by rooted cuttings was first done by Mogens N. Olesen in the nursery in Fredensborg, Denmark in July, 2013. This initial and other subsequent asexual propagations conducted in controlled environments have demonstrated that the characteristics of 'Poulren031' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren031'.

Specifically illustrated in FIG. 1 of the drawings are open flowers, a cluster of flowers on a branch, petals detached, sepals detached revealing reproductive flower parts.

Figure 1:
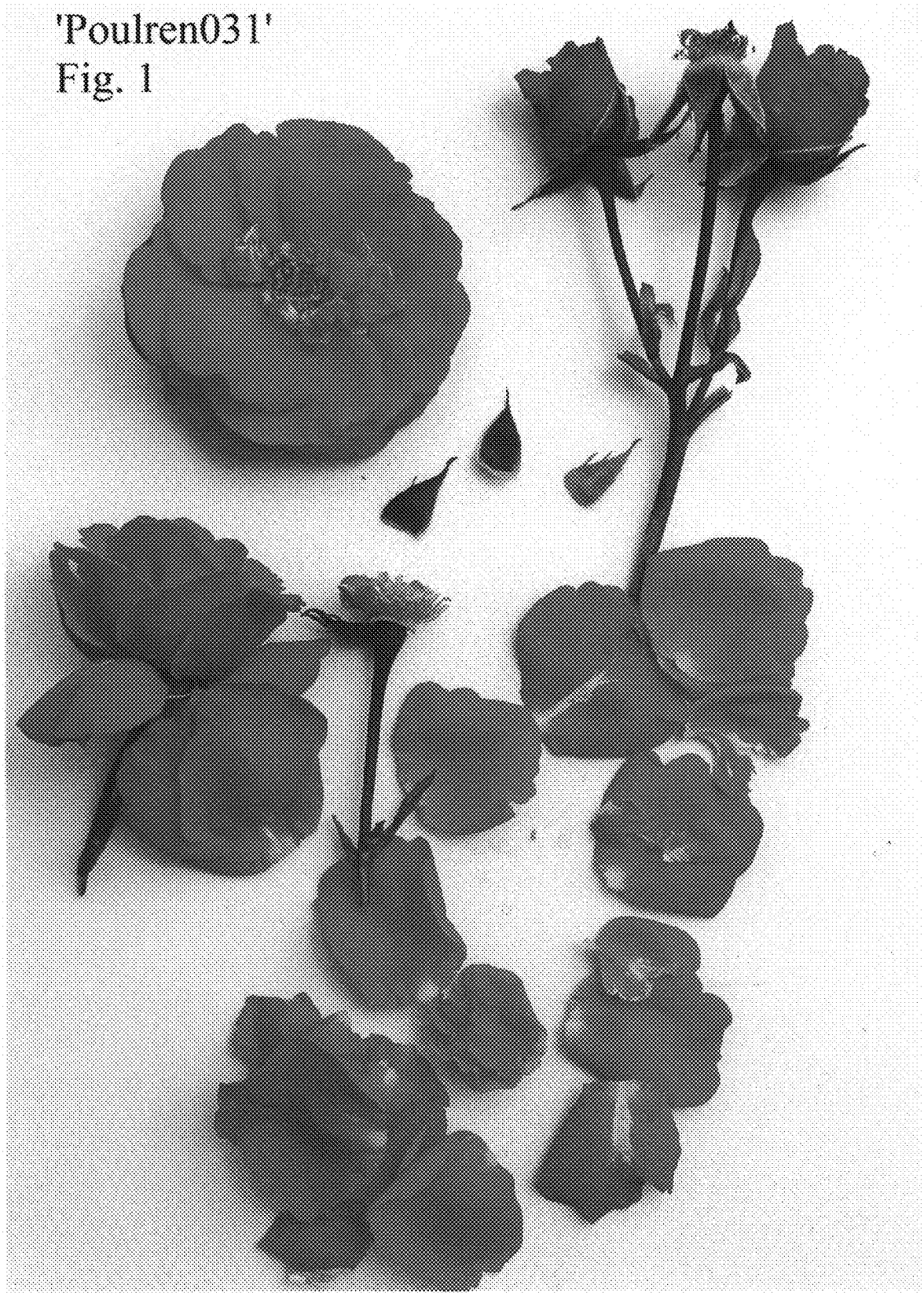
Figure 2:
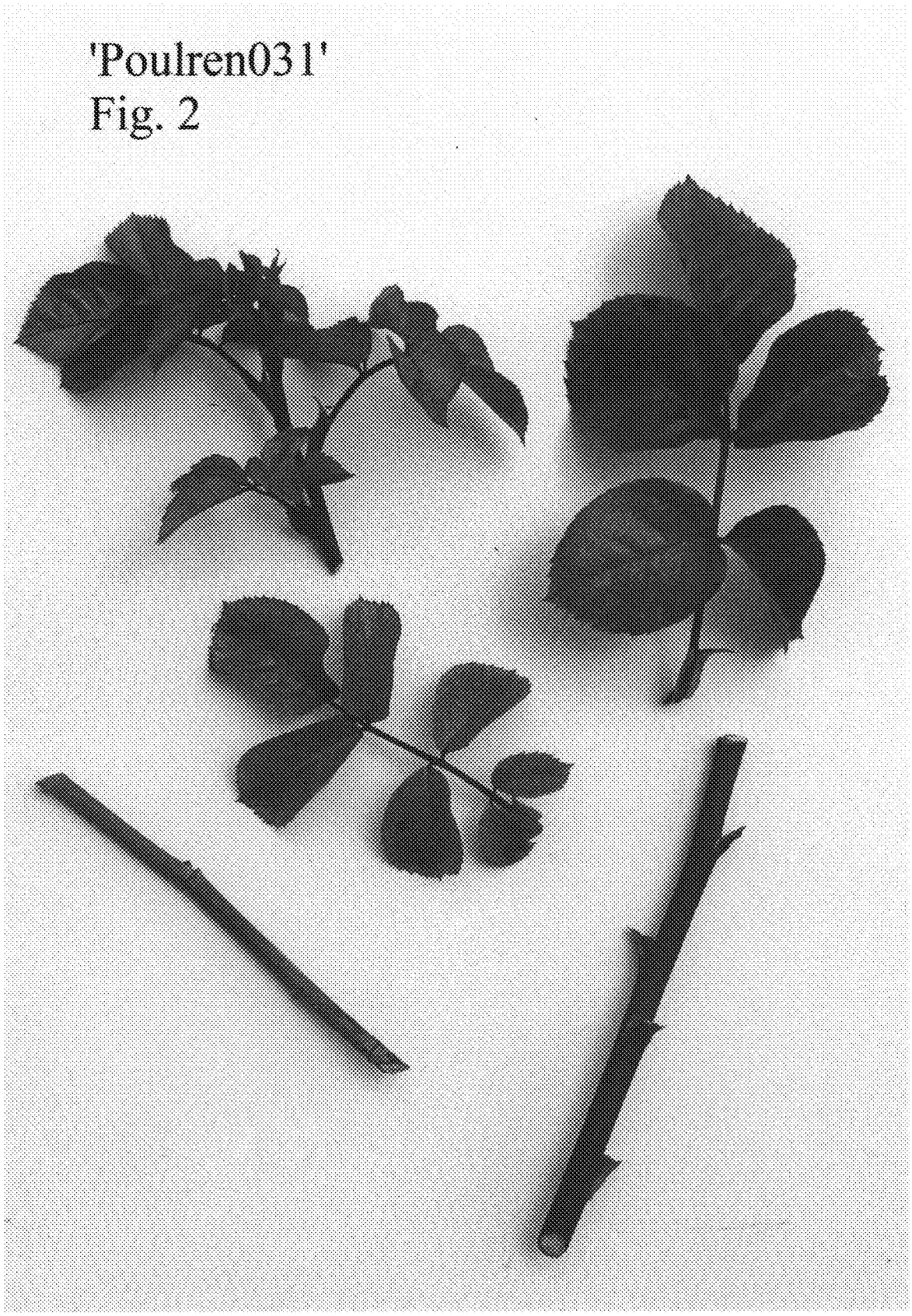

Specifically illustrated in FIG. 2 of the drawings are juvenile and mature leaves and bare stems. Plants shown are 2 years of age.

DETAILED DESCRIPTION OF THE VARIETY

The following is a description of 'Poulren031',as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulht007', U.S. Plant Pat. No. 24,806 are compared to 'Poulren031' in Chart 1.

CHART 1

| | 'Poulren031' | 'Poulht007' |
|---|---|---|
| Petal Count | 25 to 30 petals | 28 petals |
| Flower Diameter | 80 to 90 mm | 70 mm |

CHART 1-continued

| | 'Poulren031' | 'Poulht007' |
|---|---|---|
| General Tonality of Flower Color | Red Group 44B | Red Group 43B |

FLOWER AND FLOWER BUD

Blooming habit: Continuous.

Flower bud:

*Size.*—Upon opening, 24 mm in length from base of receptacle to end of bud. Bud diameter is 14 mm.

*Bud form.*—Ovoid.

*Bud color.*—As sepals divide petals are Orange-Red Group N34A and Red Group 43A.

*Sepal inner surface.*—Color: Yellow-Green Group 146D. Surface: Lightly pubescent.

*Sepal outer surface.*—Color: Yellow-Green Group 144A with dark intonations of Greyed-Purple Group 183A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—25 mm long, 11 mm wide.

*Receptacle.*—Texture: Smooth. Size: 10 mm in height, 7 mm wide. Color: Green Group 138A with intonations of Greyed-Purple Group 183A. Shape: Campanulate.

*Pedicel.*—Surface: Smooth. Length: 55 to 65 mm. Diameter: 4 mm on average. Color: Greyed-Purple Group 183B. Strength: Strong.

*Peduncle.*—Length: 2 to 5 cm. Diameter: 4 to 5 mm. Color: Yellow-Green Group 145A. Texture: Smooth.

Flower bud development: Flower buds are borne single or in clusters of about 7 flower buds per stem. Development as a panicle.

Flower bloom:

*Fragrance.*—Strong perfume.

*Duration.*—The blooms have a duration on the plant of approximately 10 days. Petals fall cleanly away from plant after flowers have fully matured.

*Size.*—Flower diameter is 80 to 90 mm when open. Flower depth is 37 mm.

*Flower shape.*—Open cup, double flower, with petals that curve out from the center.

*Shape of flower, side view.*—The upper portion is convex. The Lower portion is flattened concave.

Petalage: Under normal conditions, flowers have about 25 to 30 petals.

General tonality of blower: Open flowers are Red Group 44B.

Petal color:

*Upon opening, outer petals.*—Upper surface: Red Group 44B. Lower surface: Red Group 45B with other intonations of Red Group 46A.

*Upon opening, inner petals.*—Upper surface: Red Group 44B. Lower surface: Red Group 45B with other intonations of Red Group 46A.

*Basal petal spots, upon opening.*—Upper surface: Yellow Group 5B. Lower surface: Yellow Group 5B.

*After opening, outer petals.*—Upper surface: Red Group 44B. Lower surface: Red Group 45B with other intonations of Red Group 46A.

*After opening, inner petals.*—Upper surface: Red Group 44B. Lower surface: Red Group 45B with other intonations of Red Group 46A.

*Basal petal spots, after opening.*—Upper surface: Yellow Group 5B. Lower surface: Yellow Group 5B.

Petals:

*Petal reflex.*—Weak.

*Margin.*—Entire and uniform. Moderate undulations.

*Shape.*—Broad and elliptic. Apex shape: Rounded. Base shape: Acute.

*Size.*—45 mm (l)×50 mm (w).

*Texture.*—Smooth.

*Thickness.*—Average.

Petaloids:

*Size.*—15 mm (l) by 7 mm (w).

*Quantity.*—About 4.

*Shape.*—Elliptical with an acute base and rounded apes.

*Color.*—

Reproductive flower parts:

*Pollen.*—None observed.

*Anthers.*—Size: 3 mm in length. Color: Yellow-Orange Group 14B. Quantity: 45 on average.

*Filaments.*—Color: Orange-Red Group N34C. Length: 8 mm.

*Pistils.*—Length: 6 mm. Quantity: 35 on average.

*Stigmas.*—Color: Greyed Yellow 161A.

*Styles.*—Color: Green White 157A.

*Location of stigmas.*—Level in location relative to the length of the filaments and the height of the anthers.

*Hips.*—None Observed.

PLANT

Plant growth: Upright. Plants are 100 cm in height, and 60 cm wide.

Stems:

*Color of juvenile growth.*—Greyed-Purple Group 183A.

*Color of mature growth.*—Yellow-Green Group 146B.

*Length.*—Canes are about 40 to 60 cm from the base of the plant to the flowering portion.

*Diameter.*—About 7 mm.

*Internodes.*—On mature canes about 55 mm between nodes.

*Surface texture.*—Young wood: Smooth. Older wood: Smooth.

Long prickles: None observed.

Plant foliage:

*Compound leaf.*—160 mm (l)×90 mm (w).

*Quantity.*—2 leaves per 10 cm of stem on average.

*Leaf bearing angle to the stem.*—45 degrees.

*Color of juvenile foliage.*—Upper side: Yellow-Green Group N144A with marginal intonations of Greyed-Purple Group 183A. Lower side: Yellow-Green Group N144A with marginal intonations of Greyed-Purple Group 183A.

*Color of mature foliage.*—Upper side: Yellow-Green Group 146A. Lower side: Yellow-Green Group 146C.

Plant leaves and leaflets:

*Stipules.*—Size: 21 mm long, 5 mm wide. Quantity: 2 per compound leaf. Shape: Linear, slightly broad based with outward extending apices. Margins: Finely serrated. Color: Yellow-Green Group 144A.

*Petiole*.—Length: 50 mm. Diameter: 3 mm. Upper surface color: Greyed-Purple Group 183A. Lower surface color: Yellow-Green Group 144A.

*Rachis*.—Length: 60 mm. Upper surface color: Greyed-Purple Group 183A. Lower surface color: Yellow-Green Group 144A.

*Leaflet*.—Quantity: Normally 5 to 7 leaflets. Margins: Serrated. Size: Terminal leaflets are about 70 mm long, 51 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Hybrid Tea rose class named 'Poulren031', substantially as illustrated and described herein, due to its abundant orange red flowers, disease resistance, and extended period of bloom.

* * * * *

'Poulren031'

'Poulren031'